United States Patent [19]

Alazet

[11] Patent Number: 5,071,628

[45] Date of Patent: Dec. 10, 1991

[54] DEVICE FOR DISINFECTION OF SOLES OF SHOES

[76] Inventor: Jean Alazet, 26, rue des Fosses-Saint-Bernard, F-75005 Paris, France

[21] Appl. No.: 423,408
[22] PCT Filed: Jan. 31, 1989
[86] PCT No.: PCT/FR89/00032
   § 371 Date: Sep. 5, 1989
   § 102(e) Date: Sep. 5, 1989
[87] PCT Pub. No.: WO89/06982
   PCT Pub. Date: Aug. 10, 1989

[30] Foreign Application Priority Data

Feb. 2, 1988 [FR] France ................... 88 01166

[51] Int. Cl.$^5$ ................... A61L 2/18; A47L 23/26
[52] U.S. Cl. ................... 422/292; 422/300; 15/215
[58] Field of Search ........... 15/215, 216; 422/120, 422/292, 297, 28, 300

[56] References Cited

U.S. PATENT DOCUMENTS 2,604,377 7/1952 Eames ................... 422/300
3,578,738 5/1971 Hughes ................... 15/215

FOREIGN PATENT DOCUMENTS 2590473 5/1987 France .

Primary Examiner—Robert J. Warden
Assistant Examiner—Howard Hampel
Attorney, Agent, or Firm—Young & Thompson

[57] ABSTRACT

A device providing a reception surface for shoe soles to be disinfected, beneath which is an element impregnated with a disinfection liquid, the complete assembly being contained in a shallow tray or reservoir which is placed on the ground or embedded in this latter. The tray or reservoir (1) contains a certain quantity of disinfection liquid (4) and above the level of this liquid is a rigid plate which bears on the bottom of the tray or reservoir, for example by means of spacer members or ribs (7). The impregnation element consists of a sheet (9) of porous material stretched over and supported by the rigid plate (5a). At least one of the edges of the sheet dips into the disinfection liquid contained in the tray or reservoir (1) and serves as a capillary wick to impregnate the sheet with disinfectant. A perforated covering element (11) covers the impregnation sheet (9) so as to constitute the receiving surface for the shoes to be disinfected.

6 Claims, 2 Drawing Sheets

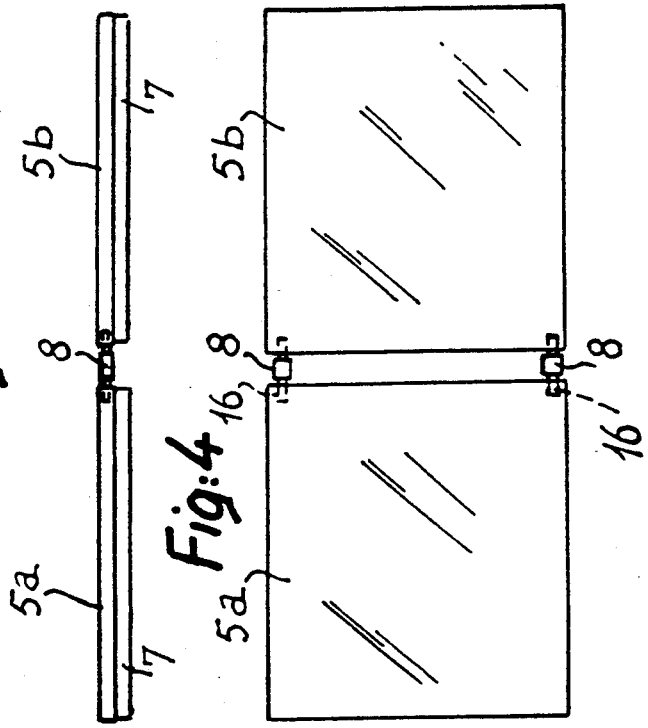
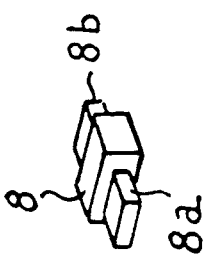
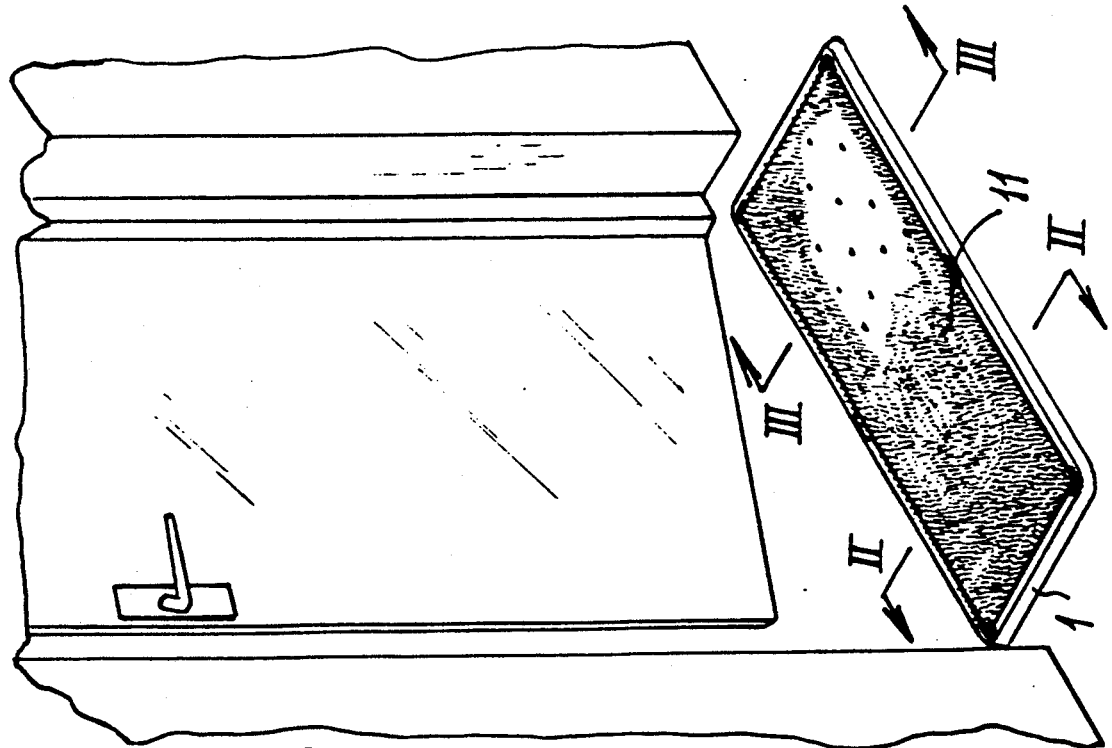

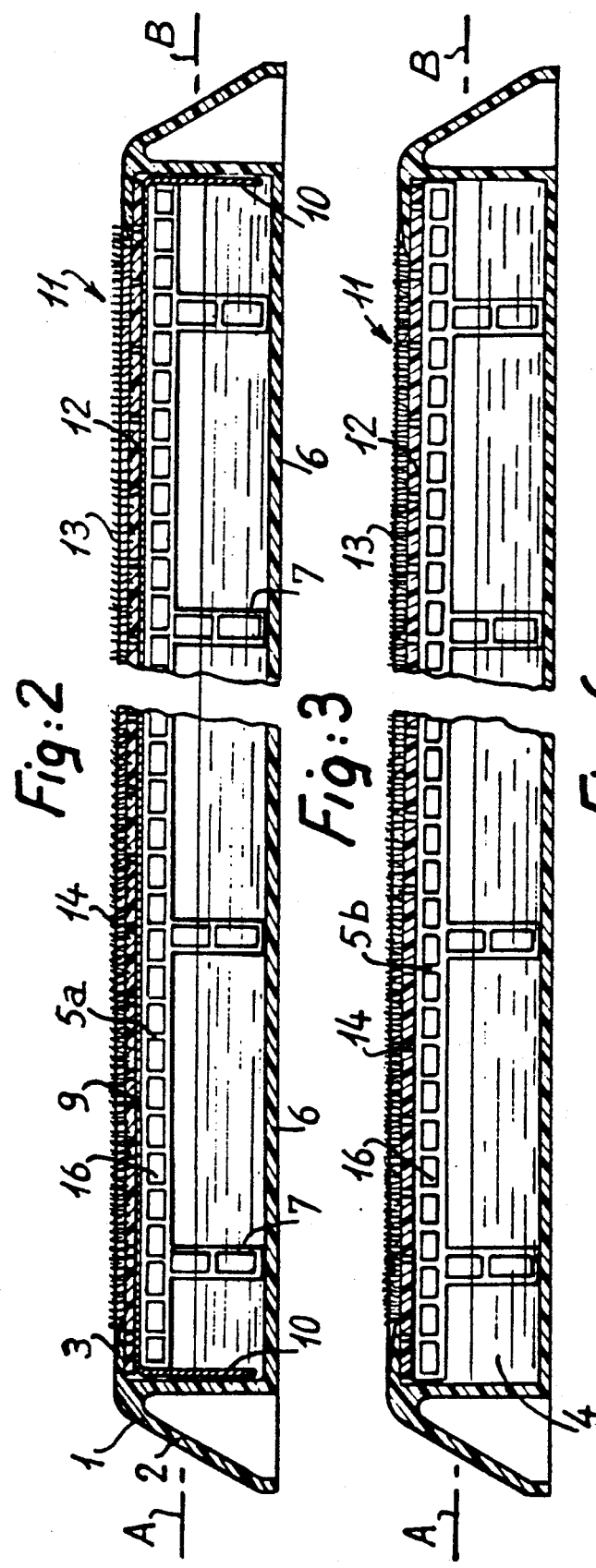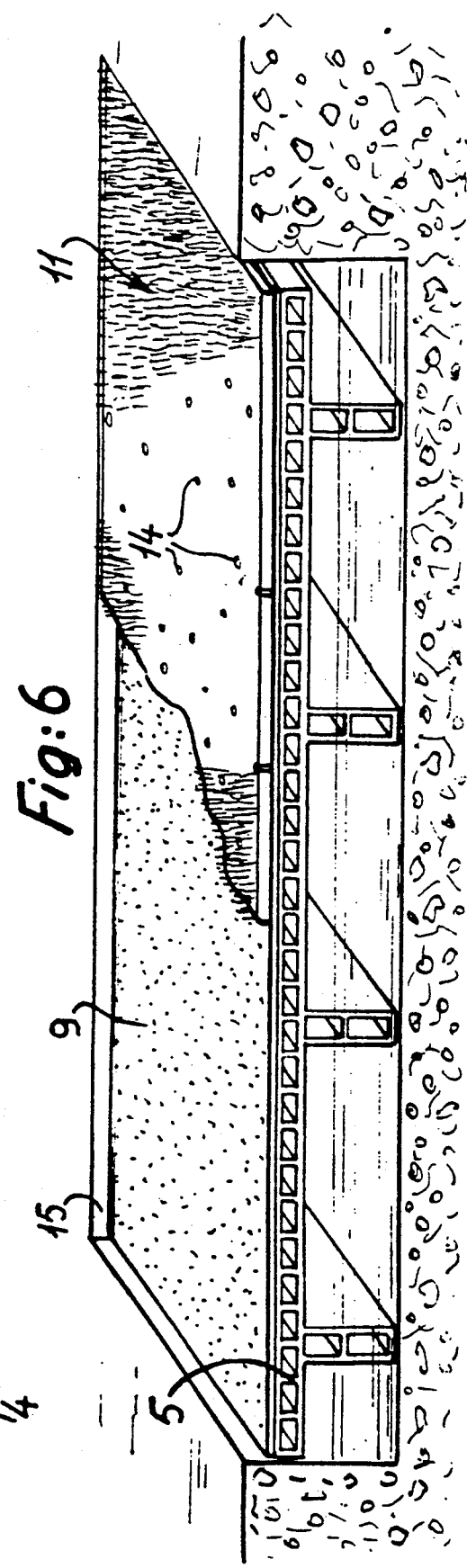

DEVICE FOR DISINFECTION OF SOLES OF SHOES

The present invention is concerned with the problem presented by the need to protect residential premises against the introduction of pathogenic agents or infectious germs carried by the soles of shoes.

In order to solve this problem, it has already been proposed to provide disinfection devices which are intended to be placed at the entrance of premises instead of an ordinary sole-wiping doormat. One of these devices, described in patent FR 2,590,473, consists of a shallow tray which is intended to be placed on the ground and contains a relatively thick body of spongy material containing a disinfectant liquid. This spongy body is covered with a net which serves as a support for bristles and which is intended to constitute the receiving surface for shoes to be disinfected. Thus, when a person places his or her shoes on this surface, the person's weight causes compression of the spongy body containing the disinfection liquid. This latter is thus abruptly expelled from said spongy body, with the result that it impregnates the soles of shoes placed on the surface of the device considered.

However, although the design of a device of this type appears satisfactory from a theoretical standpoint, this is absolutely not the case from a practical point of view. In fact, with the solution thus contemplated, an excessive quantity of liquid is discharged onto the soles of shoes. This has a disadvantage in that it gives rise to excessive consumption of said liquid and consequently to the need for frequent re-supply of the spongy body with disinfection liquid. Moreover, when the shoes are too strongly impregnated, they are liable to produce stains and dirty marks on the floor of the corresponding premises, especially when this floor is covered with wall-to-wall carpet.

Moreover, by reason of the abruptness of compression of the spongy body under the action of a person's weight, upward squirting of the disinfection liquid frequently occurs. This results in dirty marks on the lower parts of clothing of the person who is standing on the device as well as on the floor and adjacent walls. This clearly constitutes an unacceptable drawback.

All the same disadvantages are again met with in the case of the device described in patent FR 2,381,152. In fact, this latter also comprises a relatively thick spongy body which is impregnated with disinfection liquid. Here again, it is the compression and deformation of said spongy body which causes expulsion of the disinfection liquid towards the soles of shoes placed on a perforated flexible sheet which covers the entire assembly.

It is for this reason that the present invention has for its object a disinfection device which is of the same general type but is so designed as to circumvent these disadvantages.

In the same manner as the devices recalled earlier, the present device comprises a reception surface for soles to be disinfected, beneath which provision is made for an element impregnated with a disinfection liquid, the complete assembly being contained in a shallow tray or the like which is intended to be placed on the ground. However, the device in accordance with the invention is characterized in that:

on the one hand the tray of this device contains a certain quantity of disinfection liquid and provision is made above the level of this liquid for a rigid plate which bears on the bottom wall of the tray, for example by means of spacer members, ribs or the like, and on the other hand the impregnation element consists of a sheet of porous material or the like stretched over the rigid plate which serves as a support for this latter, and at least one of the edges of said sheet dips into the disinfection liquid contained in the tray, a perforated covering element or the like being placed over said impregnation sheet so as to constitute the reception surface for shoes to be disinfected.

Thus impregnation of shoe soles takes place by simple moistening as a result of rubbing contact with the reception surface which has already been moistened by the disinfection liquid, and not by abrupt expulsion of said liquid from a spongy body of substantial thickness under the action of compression of this latter. Furthermore, by virtue of the design concept of the device in accordance with the invention, the reception surface for soles to be disinfected is virtually isolated from the disinfection liquid which is contained in the bottom of the tray, namely by means of the rigid plate which serves as a support for the porous impregnation sheet. In this connection, emphasis should be laid on the fact that this sheet does not constitute a spongy body of substantial thickness but a relatively thin sheet which is only impregnated by capillarity with the disinfection liquid and which contains a very limited quantity of this liquid. It is for this reason that there is no risk of abrupt expulsion of a large quantity of disinfection liquid under the weight of a person.

In a particular form of construction of the present device, this latter is so designed that it can be installed directly within a cavity formed in the ground, for example a cavity already provided for positioning a conventional wiping doormat, or a cavity specially arranged to receive the present device. In this particular form of construction, this latter is accordingly simply constituted by a rigid plate for supporting the impregnation sheet as well as by the element which covers the complete assembly. In such a case, in fact, the disinfection liquid is directly placed within the cavity which is provided in the ground and which accordingly performs the function of a disinfection liquid reservoir in the same manner as the tray which existed in the preceding form of construction.

However, other particular features and advantages of the device in accordance with the invention will become apparent from the following description which is given with reference to the accompanying drawing solely by way of indication.

In this drawing:

FIG. 1 is a view in perspective illustrating the installation of the disinfection device in accordance with the invention in a doorway located at the entrance of predetermined premises.

FIGS. 2 and 3 are transverse sectional views of said device, respectively along the lines II—II and III—III of FIG. 1 but to a different scale.

FIG. 4 is a top view of the two rigid plates provided within the corresponding device.

FIG. 5 is an end view in elevation of said two plates.

FIG. 6 is a longitudinal sectional view of another form of construction of the disinfection device in accordance with the invention.

FIG. 7 is a perspective view of a special part provided in the first form of construction.

In the example shown in FIGS. 1 to 5, the present disinfection device comprises a rectangular tray 1 of small thickness which virtually constitutes the body of this device. This tray can be laid flat on the ground or else can be fitted in a recess formed in the ground for this purpose in order that its top surface should be flush with the ground. Said tray can advantageously be manufactured by moulding from plastic material or elastomer.

The peripheral wall 2 surrounding said tray can be inclined as is apparent from FIG. 2. The top edge of said wall has a horizontal flange 3 which extends inwards.

The tray 1 contains a certain quantity of disinfection liquid 4 which is capable of destroying pathogenic agents and infectious germs. This liquid can fill at least half the height of the tray 1, its maximum level being indicated by the line A-B. Above this latter are provided two horizontal rigid plates 5a and 5b which are placed one after the other in the lengthwise direction and the overall surface area of which corresponds to that of the internal space of the tray 1. These two plates are directly supported on the bottom wall 6 of the tray 1 by means of spacer members or ribs 7 which project downwards from the bottom surface of said plates and are intended to bear on the bottom wall of the tray 1 and which extend in the longitudinal direction. In the example shown in FIGS. 1 to 5, each of these plates is fabricated from extrusion-moulded plastic material and is provided with a series of parallel compartments 16 which extend in the longitudinal direction. However, ribs 7 as well as the compartments 16 could just as easily extend in the transverse direction. The height of said ribs 7 is such that the plates 5a and 5b are accordingly located above the level of the line A-B.

However, the ribs 7 could be replaced by any other suitable supporting elements such as, for example, studs or other spacer members. If so required, the ribs or other spacer members carried by the bottom faces of the plates 5a and 5b could be replaced by projecting studs or other supporting elements provided on the top face of the bottom wall 6 of the tray 1.

Preferably, the two plates 5a and 5b are spaced apart (see FIG. 4). However, they are connected to each other by means of junction members 8, the ends 8a and 8b of which are engaged within recesses 16 existing in the plates 5a and 5b (see FIG. 4). However, any other suitable elements could be employed for attaching the two plates 5a and 5b to each other.

One of these two plates, namely the plate 5a, is covered with a thin sheet 9 of porous material which can be soaked with the disinfection liquid. This sheet covers the entire surface of the plate 5a but at least one of its edges extends beyond and is turned downwards in order to dip into the disinfection liquid contained in the tray 4. In the example shown in FIG. 2, both longitudinal edges 10 of said porous sheet are turned downwards and dip into the liquid 4. The turned-down edges perform the function of wicks so that the entire surface of the porous sheet 9 is impregnated with disinfection liquid by capillarity. However, the quantity of said impregnation liquid is very limited since the impregnation element is a porous sheet 9 of very small thickness and not a relatively thick spongy body.

In regard to the second plate 5b, it is not provided with any impregnation element of this type. However, said plate as well as the first plate 5a is covered with a brush-type mat 11 which covers both plates. Said brush mat is constituted by a thin layer 12 of plastic which carries a large number of bristles 13 of synthetic material or vegetable material. In addition, the bottom layer 12 has a multitude of holes 14 for allowing the liquid which impregnates the porous sheet 9 to pass through.

By virtue of the design concept of the present device, that portion of the mat 11 which covers the first plate 5a is continuously moistened by capillarity by the disinfection liquid which impregnates the porous sheet located underneath. In consequence, when a person rubs the soles of his or her shoes on this portion of the mat 11, these latter are impregnated simply by moistening with a limited quantity of disinfection liquid. Furthermore, no projection of a large quantity of said liquid is liable to take place since, contrarily to what occurs in the prior art devices recalled earlier, there is not any compression of a thick spongy body and abrupt expulsion of a liquid contained in this latter. In fact, in the case of the present device, the plate 5a isolates the porous sheet 9 from the liquid and only the edges of said sheet dip into this liquid. In consequence, said sheet does not itself serve as a disinfection liquid reservoir as is the case in the prior art devices in question. It serves simply as an impregnation element and itself contains only a very limited quantity of liquid by virtue of the very fact that it has a small thickness. Furthermore, there cannot take place a substantial deformation of said impregnation sheet since its thickness is limited and said sheet is directly supported by the rigid plate 5a provided for this purpose. In consequence, all the disadvantages of the prior art devices are thus radically removed.

In regard to that portion of the mat 11 which covers the second plate 5b, it remains dry since no provision is made beneath said portion for any porous impregnation sheet. In consequence, this portion of the mat 11 can serve as a brush for wiping shoe soles after they have been impregnated with the disinfection liquid. As will be readily apparent, suitable indications can be marked on the surface of the mat 11 in order to differentiate the two separate portions of this latter.

It should be noted that the spacing provided between the two plates 5a and 5b is intended to prevent the portion of the mat 11 which is located above the second plate 5b from being moistened by the impregnation liquid contained in the porous sheet 9.

There may preferably be provided on one side of the tray 1 a transparent plug which serves to check the level of liquid 4 contained within this latter in order to carry out a fresh filling operation whenever necessary. This filling operation can accordingly be performed through an orifice specially provided for this purpose. However, it is also possible to remove the top mat and the two plates 5a and 5b in order to carry out this filling operation. To this end, the top flange 3 of the tray 1 is flexible and its bottom edge has a number of recesses for easily lifting said flange.

The device in accordance with the invention can form the subject of many other forms of construction. This device may accordingly be constructed so as to constitute solely a surface for impregnating shoe soles whereas wiping of these soles is carried out on another suitable surface, for example on a conventional doormat. In such a case, the device in accordance with the invention comprises a rigid plate in a single piece and its entire surface is covered with a porous sheet 9, at least one edge of which is turned-down so as to dip into the disinfection liquid 4 contained within the tray 1.

FIG. 6 illustrates another form of construction which is designed to be employed directly within a cavity 15 formed in the ground, for example a cavity already provided for the installation of a conventional doormat or a cavity specially designed for the installation of the device in accordance with the invention. In such a case, the tray 1 provided in the preceding form of construction is completely suppressed. The device is in this case simply constituted by the two plates 5a and 5b as well as by the porous impregnation layer 9 which covers the first of these plates and the mat 11 placed over the complete assembly. However, the example shown in FIG. 6 corresponds to the alternative embodiment in which provision is made for a single plate 5 instead of two separate and distinct plates 5a and 5b. Said single plate is covered with a porous sheet 9 which extends over its entire surface and the same applies to the top mat 11. In this case, the entire top surface of the present device serves as a surface for impregnating shoe soles which must subsequently be wiped on another suitable surface.

After its installation within the cavity 15, the plate 5 is directly applied against the bottom of this latter by means of the ribs 7 provided on the underface of said plate. In view of the fact that the tray is completely suppressed, the impregnation liquid 4 is poured directly into the interior of the cavity 15 which thus serves as a reservoir. Under these conditions, the cavity walls can advantageously be covered beforehand with a fluid-tight lining. As will readily be apparent, the cavity 15 must not be filled to the level of the plate 5 in order that this latter should be capable of performing the same function as the plates 5a and 5b of the preceding form of construction.

Thus the operation of this device is the same as before. In fact, impregnation of the porous sheet 9 takes place simply by capillarity by reason of the fact that at least one edge of said sheet dips into the disinfection liquid contained in the cavity 15. Here again, impregnation of shoe soles to be disinfected takes place simply by moistening and not by projection of a liquid contained within a relatively thick spongy body which is subjected to a high degree of compression.

It is worthy of note that the single plate 5 or the two separate and distinct plates 5a and 5b can be readily cut to the dimensions of the cavity 15 if a cavity already exists in the ground.

Once again, however, the device in accordance with the invention may form the subject of many other forms of construction, especially according to cases and applications.

I claim:

1. Device for the disinfection of shoe soles, comprising a reservoir containing disinfection liquid, a rigid horizontal plate disposed above the level of the disinfection liquid and resting on the bottom of the reservoir, a sheet of porous material extending over the rigid plate and having an edge immersed in the disinfection liquid to serve as a wick to impregnate the porous sheet with disinfection liquid, and a perforated covering element disposed over the impregnation sheet and providing a reception surface for shoe soles to be disinfected.

2. A device as claimed in claim 1, said rigid plate having spacer members on its underside which extend down and rest on the bottom of the reservoir.

3. A device as claimed in claim 1, the reservoir being constituted by a cavity formed in the ground.

4. A device as claimed in claim 1, said reservoir being constituted by a basin resting on the ground.

5. A device as claimed in claim 1, the plate being in two parts only one of which is covered by the impregnation sheet, the covering element covering both plates.

6. A device as claimed in claim 5, said plates being spaced edgewise from each other, and junction members edgewise interconnecting the two plates.

* * * * *